United States Patent [19]
Carter et al.

[11] Patent Number: 5,814,615
[45] Date of Patent: Sep. 29, 1998

[54] ANTIBIOTIC LL-E19020 ALPHA$_1$

[75] Inventors: Guy Thomas Carter, Suffern; David R. Williams, Stony Point; Joseph D. Korshalla, Pearl River, all of N.Y.

[73] Assignee: Roche Vitamins Inc., Parsippany, N.J.

[21] Appl. No.: 756,646

[22] Filed: Sep. 9, 1991

[51] Int. Cl.$^6$ .............................. A61K 31/70; C07H 3/06
[52] U.S. Cl. ............................................. 514/25; 536/16.8
[58] Field of Search .................................. 536/16.8, 18.1, 536/18.7, 25; 514/25.23; 424/122

[56] References Cited

U.S. PATENT DOCUMENTS

| | | | |
|---|---|---|---|
| 4,704,276 | 11/1987 | Kantor | 424/122 |
| 4,705,688 | 11/1987 | Carter et al. | 424/122 |
| 4,968,493 | 11/1990 | Carter et al. | 424/122 |

FOREIGN PATENT DOCUMENTS

| 442783 | 8/1991 | European Pat. Off. | 424/22 |
|---|---|---|---|

OTHER PUBLICATIONS

Journal of Antibiotics, 41 (10), 1511–1514 (1988).
Journal of Antibiotics, 42 (10), 1489–1493 (1989).
Journal of Chromatography, 484, 381–390 (1989).
Journal of Antibiotics, 41(10), 1293–1299 (1988).
Journal of Antibiotics, 41(10), 1300–1315 (1988).
Journal of Antibiotics, 39(10), 1361–1367 (1986).
Journal of Antibiotics, 42(1), 94–101 (1989).
Antimicrobial Agents and Chemotherapy, 33 (3), 322–325 (1989).
Program and Abstracts of the 27th Interscience Conference on Antimicrobial Agents and Chemotherapy, No. 995, p. 270, New York, Oct. 4–7 1987.
R. D. Guthrie et al., *An Introduction To The Chemistry Of Carbohydrates* p. 19 (1964).

*Primary Examiner*—Gary L. Kunz
*Attorney, Agent, or Firm*—George W. Johnston; William H. Epstein; John P. Parise

[57] ABSTRACT

The invention provides an antibiotic designated LL-E19020 Alpha$_1$ which is derived from the micro-organism *Streptomyces lydicus ssp. tanzanius* NRRL 18036.

3 Claims, 5 Drawing Sheets

ANTIBIOTIC LL-E19020 ALPHA$_1$

BACKGROUND OF THE INVENTION

1. Field of the Invention

The invention relates to a new antibiotic designated LL-E19020 Alpha$_1$, to its production by fermentation and to a process for its recovery and purification.

2. Description of the Prior Art

Antibiotics LL-E19020 Alpha and LL-E19020 Beta are disclosed in U.S. Pat. No. 4,705,688, The Journal Of Antibiotics, 41(10), 1511–1514 (1988) and The Journal Of Antibiotics, 42(10), 1489–1493 (1989). Antibiotic LL-E19020 Alpha has a phenylacetate ester group attached at C-23 and has the structure:

Antibiotic LL-E19020 Beta has a phenylacetate ester group attached at C-24 and has the structure:

A process for purification of the antibiotic LL-E19020 Alpha by reversed phase HPLC purification is described in J. of Chrom. 484,381–390 1989. Antibiotics LL-E19020 Alpha and LL-E19020 Beta are also useful for increasing the growth rate of meat producing animals and for treating respiratory disease, fowl cholera and necrotic enteritis as described in U.S. Pat. No. 4,704,276 and U.S. Pat. No. 4,968,493.

A related family of compounds, the phenelfamycins, is reported in The Journal Of Antibiotics, 41(10), 1293–1299 (1988); The Journal Of Antibiotics, 41(10), 1300–1315 (1988); The Journal Of Antibiotics, 39(10), 1361–1367 (1986); The Journal Of Antibiotics, 42(1), 94–101 (1989); Antimicrobiol Agents and Chemotherapy, 33(3), 322–325 (1989); Program and Abstracts Of The 27th Interscience Conference on Antimicrobial Agents Chemotherapy, No. 995, p 270, New York, Oct. 4–7 1987.

SUMMARY OF THE INVENTION

A new antibiotic designated LL-E19020 Alpha$_1$ has now been found. The antibiotic LL-E19020 Alpha$_1$ is the C-21 epimer of known antibiotic LL-E19020 Alpha.

The physico chemical characteristics of LL-E19020 Alpha$_1$ are as follows:

1. Molecular weight: 1225 (FABMS=M/Z 1248 corresponding to [M+Na]+)

2. Molecular formula: $C_{65}H_{95}NO_{21}$ HRFABMS: [M+Na+]+=M/Z 1248.6316 (calc. 1248.6294)
3. Ultraviolet Absorption Spectrum as shown in FIG. I. UV absorption [MeOH]λ max: 233 nm 289 nm
4. IR absorption spectrum as shown in FIG. II. IR absorption spectrum [KBr]ν max: 3439, 2974, 2932, 2830, 1715, 1647, 1618, 1454, 1367, 1258, 1191, 1150, 1093, 1023, 1007, 987 $cm^{-1}$.
5. Proton $^1H$ NMR[$CDCl_3$]: Spectrum (300 MHz) as shown in FIG. III.
6. Carbon 13 $^{13}C$ NMR[$CDCl_3$] Spectrum as shown in FIG. IV, significant peaks listed below (δ from TMS): 171.8, 171.1, 170.4, 146.0, 140.4, 137.0, 134.4, 134.0, 132.1, 130.2, 129.7, 129.7, 129.0, 128.8, 128.8, 128.7, 128.6, 128.3, 128.1, 127.8, 127.5, 127.0, 120.5, 100.6, 99.02, 98.15, 96.69, 89.13, 83.12, 81.62, 77.72, 74.42, 77.19, 74.65, 74.37, 74.37, 74.27, 73.06, 72.16, 69.14, 67.52, 66.56, 66.01, 64.96, 56.55, 56.10, 55.71, 55.48, 50.35, 42.21, 41.63, 39.98, 39.26, 38.38, 32.91, 31.12, 29.88, 23.66, 18.09, 17.24, 16.99, 14.65, 13.49, 10.89, 10.20.
7. High pressure liquid chromatography (HPLC) retention time of 23.1 minutes using a gradient of dioxane in aqueous acetic acid.

The new antibiotic LL-E19020 Alpha$_1$ is formed along with LL-E19020 Alpha and LL-E19020 Beta during cultivation under controlled conditions of a strain of *Streptomyces lydicus SSP. tanzanius*, NRRL 18036. The new antibiotic LL-E19020 Alpha$_1$ is separated from LL-E19020 Alpha and LL-E19020 Beta and subsequently purified by high pressure liquid chromatography (HPLC).

BRIEF DESCRIPTION OF THE DRAWINGS

FIG. I shows the ultraviolet absorption spectrum of LL-E19020 Alpha$_1$.

FIG. II shows the infrared absorption spectrum of LL-E19020 Alpha$_1$.

FIG. III shows the proton nuclear magnetic resonance spectrum of LL-E19020 Alpha$_1$.

FIG. IV shows the carbon-13 nuclear magnetic resonance spectrum of LL-E19020 Alpha$_1$.

DESCRIPTION OF THE PREFERRED EMBODIMENTS

Figure 1:
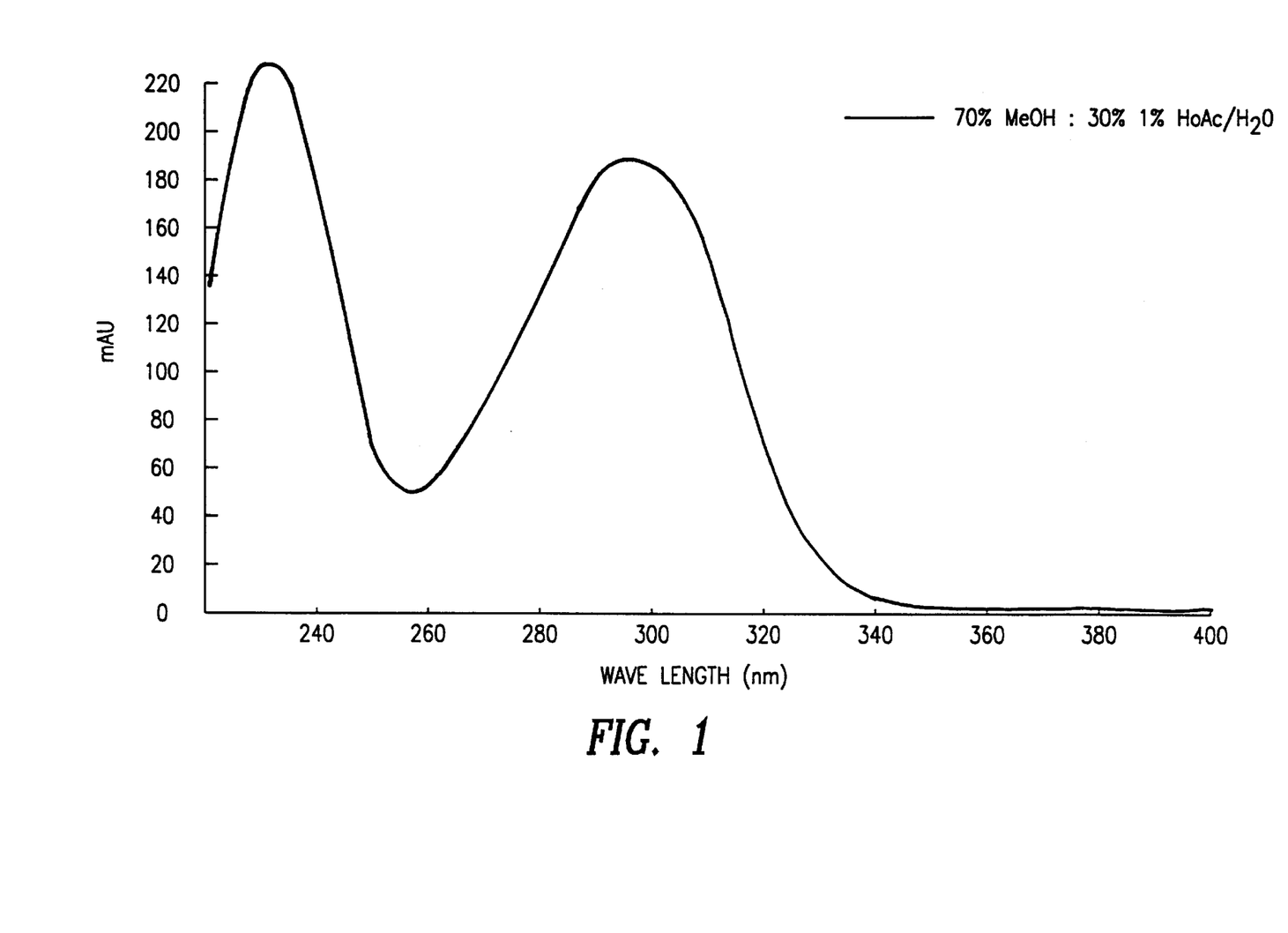
Figure 1C:
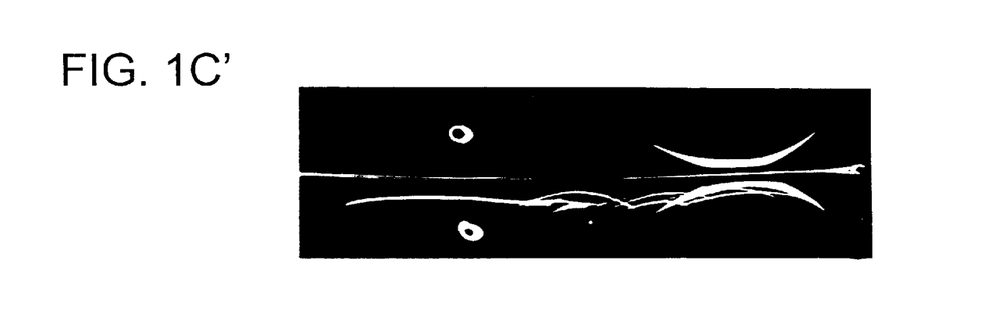
Figure 2:
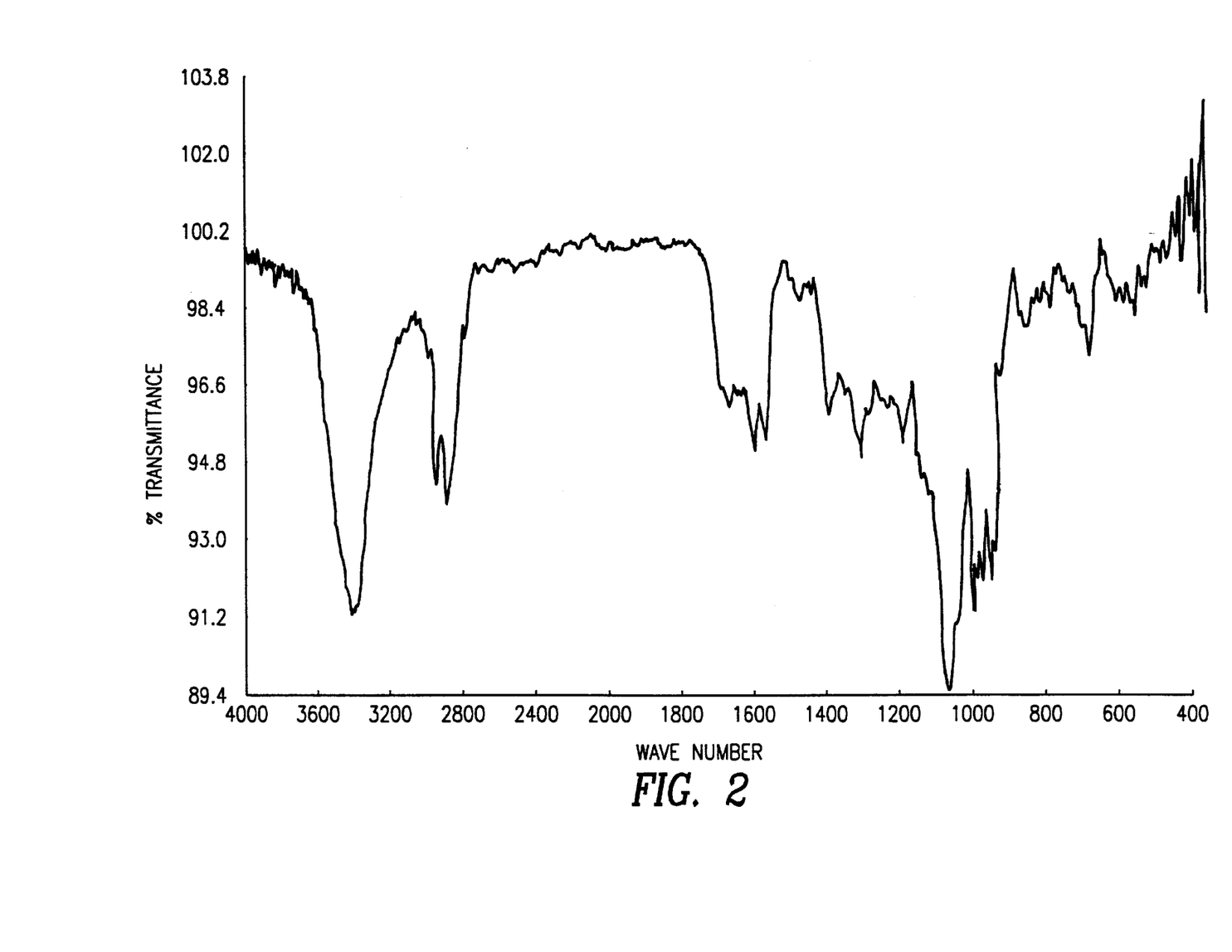
Figure 3:
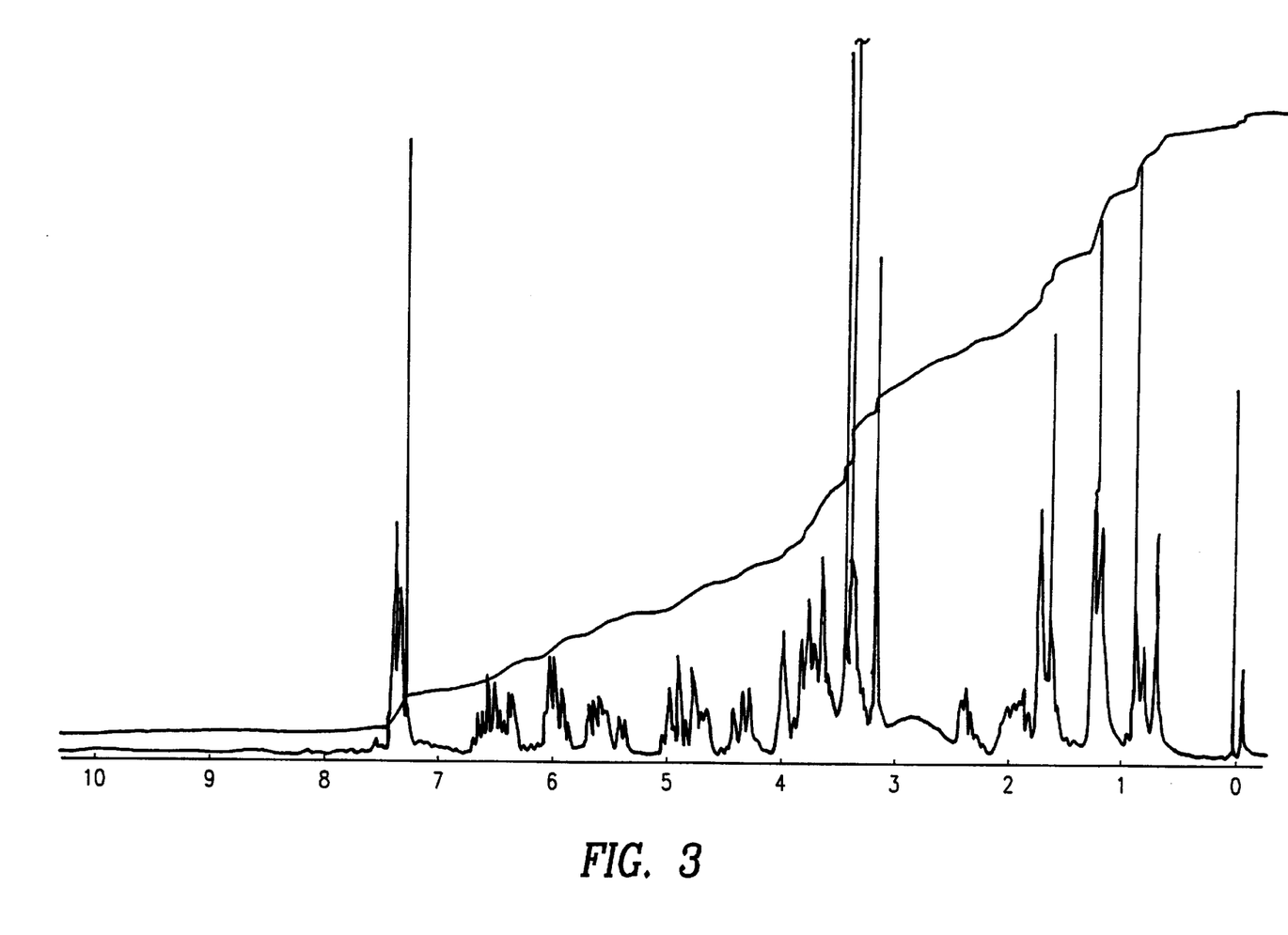
Figure 4:
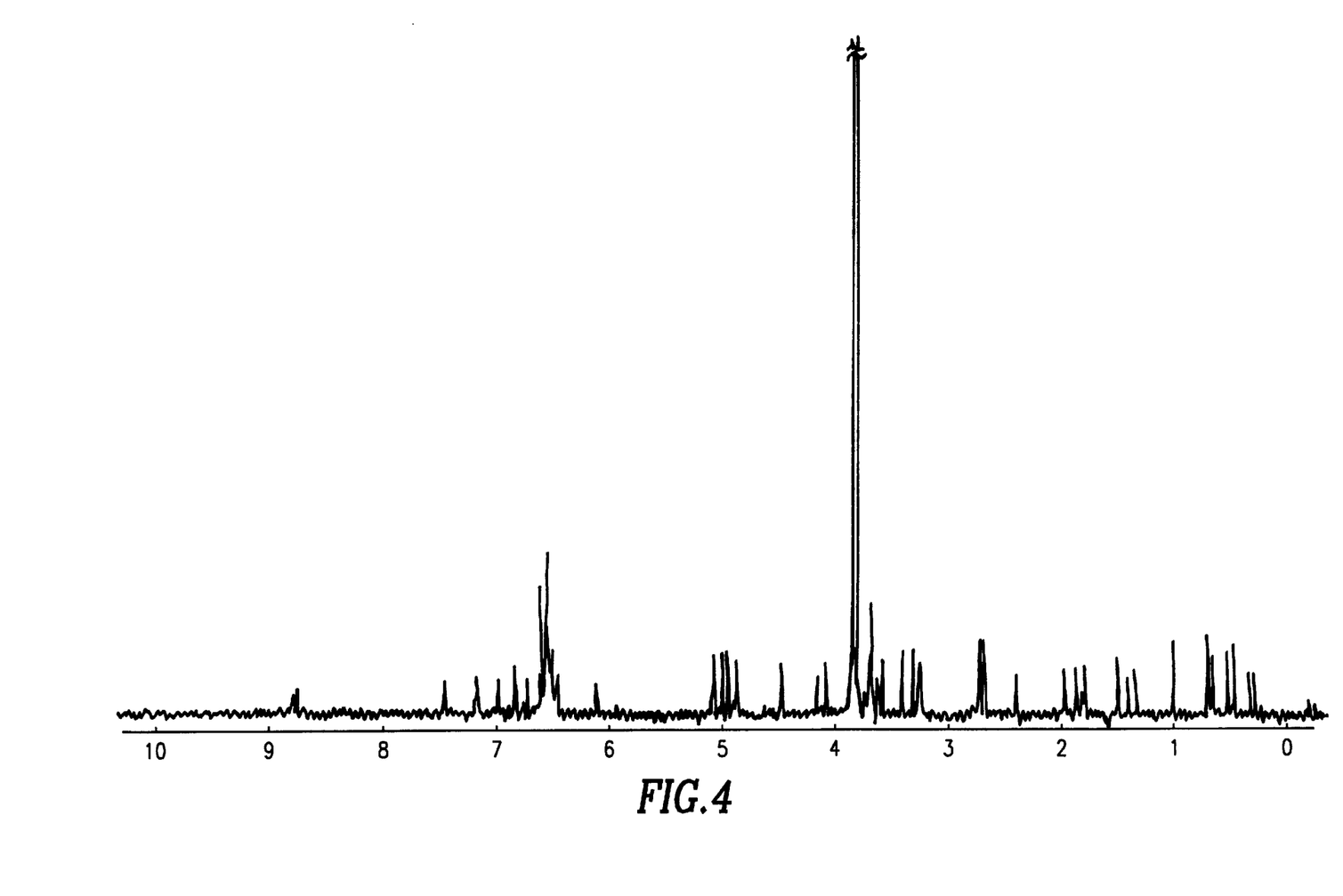

The antibiotic LL-E19020 Alpha$_1$ is produced by fermentation of a strain of *Streptomyces lydicus, SSP. tanzanius*, NRRL 18036, in an aqueous nutrient medium containing assimilable sources of carbon and nitrogen under submerged aerobic conditions. This microorganism is maintained in the culture collection of the Medical Research Division, American Cyanamid Company, Pearl River, N.Y. as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, reffinose, rhamnose, sucrose and xylose. Cellulose is not utilized.

The reactions of LL-E19020 in the Gordon Physiological Series are compared in the following Table I with those of *Streptomyces lydicus* ISP 5461 which it most closely resembles morphologically and physiologically.

Because LL-E19020 differs from ISP 5461 in five(5) characteristics (xanthine hydrolysis, decarboxylation of oxalate, acid from erythritol, rhamnose and β-methyl-D-xyloside) it is designated as a subspecies of *Streptomyces lydicus*.

TABLE I

Gordon Test Reactions Of LL-E19020 And *Streptomyces lydicus* ISP 5461

| Reactions | LL-E19020 | ISP 5461 |
|---|---|---|
| Degradation/Transformation of | | |
| Casein | + | + |
| Xanthine | − | + |
| Hypoxanthine | + | + |
| Tyrosine | + | + |
| Adenine | + | + |
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% Sodium chloride | + | + |
| Salicylate | − | − |
| Lysozyme Broth | trace | trace |
| Utilization of | | |
| Acetate | + | + |
| Benzoate | + | + |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arbinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sobitol | + | + |
| Sucrose | + | + |

TABLE I-continued

Gordon Test Reactions Of LL-E19020
And *Streptomyces lydicus* ISP 5461

| Reactions | LL-E19020 | ISP 5461 |
|---|---|---|
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure of X-radiation, ultraviolet radiation, N'-methyl-N'-nitro-N-nitrosoguanidine, actinophages and the like.

Cultivation of *Streptomyces lydicus ssp. tanzanius* NRRL 18036 may be carried out in a wide variety of liquid culture media. Media which are useful for the production of LL-E19020 Alpha$_1$ include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

The antibiotic LL-E19020 Alpha$_1$ is recovered from the fermentation broth by pH adjustment to 4.5–5.5, filtration through diatomaceous earth, extraction into a solvent such as ethyl acetate, concentration, dissolution in a solvent such as dichloromethane and purification by column chromatography on silica gel using successively, dichloromethane and methanol:dichloromethane (1:4), giving a crude product. The crude product is further purified by high performance liquid chromatography on a reverse-phase column using the system of 52.5% dioxane: 47.5% 1% acetic acid or 3150:2850:60 dioxane:water:acetic acid. The invention will be further described in conjunction with the following non-limiting examples.

EXAMPLE 1

Inoculum Preparation

A typical medium used to grow the primary inoculum is prepared according to the following formula:

| | | |
|---|---|---|
| Dextrose | 1.0% | |
| Dextrin | 2.0% | |
| Yeast extract | 0.5% | |
| NZ Amine A | 0.5% | |
| Calcium carbonate | 0.1% | |
| Water qs | 100.0% | |

NOTE: NZ Amine A is a pancreatic digest of casein, registered trademark of Scheffield Chemical, Norwich, N.Y.

This medium is adjusted to pH 7.0 and then sterilized. A 100 ml portion of this sterile medium in a 500 ml flask, is inoculated with mycelial scrapings from an agar slant of *Streptomyces lydicus ssp. tanzanius* NRRL 18036. The medium is then placed on a rotary shaker and incubated at 28° C. for 48 hours. This primary inoculum is then used to inoculate 10 liters of the same sterile medium in a bottle. This is grown for 24 hours providing secondary inoculum. This secondary inoculum is then used to inoculate 250 liters of the same sterile medium in a tank. This medium is grown at 28° C. for 48 hours with a sterile air flow of 200 liters per liter of mash per minute and agitation by an impeller driven at 220 rpm, providing tertiary inoculum.

EXAMPLE 2

Fermentation

A fermentation production medium of the following formulation is prepared:

| | |
|---|---|
| Dextrin | 3.0% |
| Molasses | 2.0% |
| Soy peptone | 0.75% |
| Yeast extract | 0.25% |
| Calcium carbonate | 0.1% |
| Water qs | 100.0% |

This medium is sterilized and 2700 liters is then inoculated with 300 liters of tertiary inoculum from Example 1. The fermentation is conducted at 28° C. with a sterile air flow of 0.55 liters of air per liter of mash per minute and agitation by an impeller driven at 100 rpm for 113 hours, at which time the mash is harvested.

EXAMPLE 3

Isolation and Purification of LL-E19020 Alpha$_1$

The harvest mash from two fermentations conducted as described in Example 2 are combined, making a total of 6000 liters, adjusted to pH 5 with hydrochloric acid and filtered through diatomaceous earth. The filtrate is extracted with ethyl acetate and the extract concentrated to a syrup.

This crude syrup is dissolved in methanol and applied to a 12 liter reverse-phase column (C18 bonded phase 40 micron). The column is eluted with acetonitrile, 0.1M ammonium acetate buffer pH 4.3 (1:1) at a rate of 1.0 liter per minute. Thirteen 24 liter fractions are collected. Fraction 7 contains impure LL-E19020α$_1$. The antibiotic is extracted from the mobile phase using dichloromethane followed by evaporation and freeze drying from t-butanol, giving a white solid.

The product of several fermentations as described above are combined to give 1700 g of solid.

Samples of this solid are purified using the following chromatographic techniques.

A 0.5 g sample is dissolved in a mixture of 4:1 dioxane/ 1% HOAC and injected onto a 2.5×50 cm C$_8$ reverse phase column. The column is eluted with 52.5% dioxane/ 47.5%:1% HOAc in water at a flow rate of 10 ml/min. After a forerun of 1100 ml, which is discarded, fractions are collected at 2.5 min intervals. Fractions are analyzed by analytical HPLC and combined. Fractions 40–48 contain E19020α$_1$.

A 0.5 g sample is dissolved in a 1:1 mixture of 4:1 dioxane/1% HOAc and 100% dioxane and injected onto a 2.5×50 cm C$_8$ reverse phase column. The column is eluted with a mixture of dioxane:water:acetic acid (3150:2850:60)

at a flow rate of 9.9 ml/min. After a brief forerun, fractions are collected at 2.5 min intervals. Fractions are analyzed by analytical HPLC and combined. Fractions 23–29 contain E19020α$_1$.

A 0.877 g sample is dissolved in a 1:1 mixture of 4:1 dioxane/1% HOAc and 100% dioxane and injected onto a 2.5×50 cm C$_8$ reverse phase column. The column is eluted with a mixture of dioxane:water:acetic acid (3150:2850:60) at a flow rate of 9.9 ml/min. After a 200 min forerun, fractions are collected from 200–230 min and contain E19020α$_1$.

A 1.0 g sample is dissolved in a 1:1 mixture of 4:1 dioxane/1% HOAc and 100% dioxane and injected onto a C$_{18}$ column (5.0×60 cm). The column is eluted with a mixture of dioxane:water:acetic acid (3150:2850:60) at a flow rate of 25 ml/min. After a forerun of 8 liters fractions are collected at 1 min intervals. Fractions are analyzed by analytical HPLC and combined accordingly: fractions 30–84 contain E19020α$_1$. The combined fractions from the above chromatographic separations are pooled and evaporated to give 200 mg which is subjected to chromatography on a C$_8$ column (2.5×50 cm) by elution with 1:1 dioxane/1% acetic acid.

The above 200 mg is dissolved in 1:1 dioxane:water and charged to the chromatography column and eluted with 1:1 dioxane/1% acetic acid at a rate of 10 ml/min. After 10.5 hours the product began to elute. Fractions are analyzed by HPLC. Fractions 40–80 are combined to afford after evaporation 18 mg of LL-E19020α$_1$.

ANALYTICAL HIGH PRESSURE LIQUID CHROMATOGRAPHY (HPLC)

The LL-E19020 Alpha$_1$ component is analyzed by analytical HPLC. Its retention time compared to LL-E19020 α and β is given in the Table below.

| COMPONENTS | | RETENTION TIME (MINUTES) SYSTEM B |
|---|---|---|
| LL-E19020α | (alpha) | 23.5 |
| LL-E19020β | (beta) | 26.7 |
| LL-E19020α$_1$ | (alpha$_1$) | 23.1 |

B. HPLC system: Alltech adsorbosphere HS 5μ C18 (4.6×250 mm) with guard column, eluted with a gradient of dioxane in 1% aqueous acetic acid. The starting composition is 55% dioxane, increasing to 70% over 25 minutes and holding at 70% for 5 minutes. The flow rate is 1.0 mL per minute.

EXAMPLE 4

In Vitro Antibacterial Activity Of LL-E19020 Alpha$_1$

The in vitro antibacterial activity of LL-E19020 Alpha$_1$ is determined against a spectrum of gram positive and gram negative bacteria by a standard agar dilution method. Mueller-Hinton agar containing 5% sheep blood and two-fold decreasing concentrations of LL-E19020 Alpha$_1$ is poured into petri dishes. The agar surfaces are inoculated with 1 to 5×10$^4$ colony forming units of bacteria by means of the Steers replicating device. The lowest concentration of antibiotic that inhibited growth of a bacterial strain after 18 hours incubation is recorded as the minimal inhibitory concentration for that strain.

Minimum Inhibitory Concentration Procedure By Agar Dilution

1. Serial two-flow dilutions of drug are prepared in Mueller-Hinton broth in a range of 2560 μg/ml-0.15 μg/ml plus a solvent control.

2. Two milliliters of drug dilution (10×) are added to sterile screw cap bottles to which 18 ml of Mueller-Hinton agar containing 5.6% defibrinated sheep blood is added. Final drug concentration ranges 256 μg/ml-0.015 μg/ml in agar containing 5% sheep blood.

3. A few isolated colonies of each test organism are inoculated into 5 ml trypticase soy broth or brain heart infusion broth. The cultures are shaken at 35° C. for 5 hours.

4. Each culture is diluted 1:50 (10$^{-1.7}$) in Mueller-Hinton broth and applied to agar plates using a Steers replicator. Control plates should be seeded last to ensure that viable organisms were present throughout the procedure. Inoculated agar plates are allowed to stand undisturbed until the inoculum spots are completely absorbed.

5. The plates are inverted and incubated at 35° C. for 18 hours with CO$_2$.

6. The minimum inhibitory concentration (MIC) is taken as the lowest concentration of antimicrobial agent at which complete inhibition of antimicrobial agent at which complete inhibition occurs. A very fine, barely visible haze or a single colony is disregarded.

The results are as follows:

IN VITRO ACTIVITY OF LL-E19020 ALPHA$_1$

MINIMAL INHIBITORY CONCENTRATION (MCG/ML)

| ORGANISM | LL-E19020-ALPHA$_1$ |
|---|---|
| 1. *Staphylococcus aureus* NEMC 87-69 | >32 |
| 2. *Staphylococcus aureus* ROSE (MP) | >32 |
| 3. *Staphylococcus aureus* IVES 6-542 | >32 |
| 4. *Staphylococcus aureus* IVES 5-160 | >32 |
| 5. *Staphylococcus aureus* IVES 5-396 | >32 |
| 6. *Staphylococcus aureus* VGH 84-47 | >32 |
| 7. *Staphylococcus aureus* CMC 83-131 | >32 |
| 8. *Staphylococcus aureus* SMITH (MP) | >32 |
| 9. *Staphylococcus aureus* K 82-26 | >32 |
| 10. *Staphylococcus aureus* ATCC 25923 | >32 |
| 11. *Staphylococcus aureus* ATCC 29213 | >32 |
| 12. *Staphylococcus haemolyticus* AVAH 88-1 | >32 |
| 13. *Staphylococcus haemolyticus* AVAH 88-3 | >32 |
| 14. *Staphylococcus epidermidis* IVES 2-455 | >32 |
| 15. *Staphylococcus epidermidis* ATCC 12228 | >32 |
| 16. *Enterococcus spp.* ARUM 87-41 | >32 |
| 17. *Enterococcus spp.* CHBM 88-60 | >32 |
| 18. *Enterococcus spp.* WRVA 88-33 | >32 |
| 19. *Enterococcus spp.* UCI 85-30 | >32 |
| 20. *Enterococcus spp.* VGH 84-69 | >32 |
| 21. *Enterococcus spp.* CMC 83-120 | >32 |
| 22. *Streptococcus pyogenes* AMCH 88-84 | 0.12 |
| 23. *Streptococcus pyogenes* AMCH 88-86 | 2 |
| 24. *Streptococcus pneumoniae* CHBM 88-75 | .5 |
| 25. *Streptococcus pneumoniae* CHBM 88-70 | 2 |
| 26. *Streptococcus pneumoniae* TEX 85-2 | 2 |
| 27. *Bacillus cereus* DAVIES | >32 |
| 28. *Kiebsiella pneumoniae* NEMC 87-271 | >32 |
| 29. *Escherichia coli* ATCC 25922 | >32 |
| 30. *Escherichia coli* ATCC 35218 | >32 |
| 31. *Escherichia coli* D-21 | >32 |
| 32. *Escherichia coli* D-22 | >32 |

As can be seen from the in vitro data above, LL-E19020 Alpha$_1$, has activity against Streptococcus.

The in vitro antibacterial activity of LL-E19020 Alpha$_1$ is also determined against a spectrum of an anaerobic bacteria.

The results are as follows:

IN VITRO ACTIVITY OF LL-E19020 ALPHA$_1$
MINIMAL INHIBITORY CONCENTRATION (MCG/ML)

| ORGANISM | E 19020 Alpha$_1$ |
|---|---|
| 1. B.fragilis ATCC 25285 | >32 |
| 2. B.vulgatus ATCC 29327 | 8 |
| 3. B.theta ATCC 29741 | >32 |
| 4. B.theta ATCC 29742 | >32 |
| 5. C.perf. ATCC 13124 | 1 |
| 6. C.diff. ATCC 17858 | 1 |
| 7. Ps. mag ATCC 29328 | ≧0.015 |
| 8. Ps. mag ATCC 14956 | ≦0.015 |
| 9. Ps. asarc. ATCC 29743 | ≦0.015 |

Antibiotic LL-E19020 Alpha$_1$ derives its utility from antibacterial activity. For example this antibiotic may be used in the suppression of bacterial infections, as a topical antibacterial agent and as a general disinfectant for laboratories.

In addition to its antibacterial activity this compound is effective as an anticoccidial agent in poultry and as a growth promotant and anthelmintic agent. These utilities are the subject of patent applications filed concurrently herewith and incorporated herein by reference.

In therapeutic use, the compound of this invention may be administered in the form of a conventional pharmaceutical composition appropriate for the intended use. Such a composition may be formulated so as to be suitable for oral, parenteral, or topical administration. The active ingredient may be combined in admixture with a nontoxic pharmaceutically acceptable carrier, which carrier may take a wide variety of forms depending on the form of preparation desired for administration, ie, oral, parenteral or topical.

When the compound is employed for the above utility, it can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

An effective amount of compound from 0.2 mg/kg of body weight to 100.0 mg/kg of body weight should be administered one to five times per day via any topical route of administration including but not limited to oral, parenteral (including subcutaneous, intravenous, intramuscular, intrasternal injection or infusion techniques), by inhalation spray, or rectally, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

This active compound may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compound is preferred.

This active compound may also be administered parenterally or intraperitoneally. Solutions or suspensions of this active compound as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

We claim:

1. A compound LL-E19020 Alpha$_1$ comprising (a) the structure

-continued (b) a molecular weight of 1225 (FABMS=M/Z 1248 corresponding to [M+Na]+);

(c) a molecular formula: $C_{65}H_{95}NO_{21}$ (d) a characteristic ultraviolet absorption spectra as shown in FIG. I of the attached drawings;

(e) a characteristic infrared absorption spectrum as shown in FIG. II of the attached drawings;

(f) a characteristic proton nuclear magnetic resonance spectrum as shown in FIG. III of the attached drawings; and (g) a characteristic carbon-13 nuclear magnetic resonance spectrum as shown in FIG. IV of the attached drawings.

(h) a characteristic HPLC retention time of 23.1 minutes using a gradient of dioxane in aqueous acetic acid.

2. A method of treating bacterial infections in warm blooded animals which comprises administering to said animals an antibacterially effective amount of antibiotic LL-E19020 $Alpha_1$ as defined in claim 1.

3. A antibiotic pharmaceutical composition which comprises an antibiotic amount of LL-E19020 $Alpha_1$ as defined in claim 1 in association with a pharmaceutically acceptable carrier.

* * * * *